United States Patent
Möschwitzer

(10) Patent No.: US 7,923,026 B2
(45) Date of Patent: Apr. 12, 2011

(54) EMBEDDED MICELLAR NANOPARTICLES

(75) Inventor: Jan Peter Möschwitzer, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 72 days.

(21) Appl. No.: 11/875,328

(22) Filed: Oct. 19, 2007

(65) Prior Publication Data

US 2009/0035368 A1   Feb. 5, 2009

Related U.S. Application Data

(60) Provisional application No. 60/853,023, filed on Oct. 20, 2006.

(51) Int. Cl.
| | |
|---|---|
| A61K 9/48 | (2006.01) |
| A61K 9/14 | (2006.01) |
| A61K 9/00 | (2006.01) |
| A61K 31/415 | (2006.01) |
| A61K 31/454 | (2006.01) |
| A61K 9/20 | (2006.01) |
| A61P 43/00 | (2006.01) |

(52) U.S. Cl. ........ 424/452; 424/489; 424/484; 424/465; 514/341; 514/406

(58) Field of Classification Search .................. 424/452
See application file for complete search history.

(56) References Cited

U.S. PATENT DOCUMENTS

| | | | | |
|---|---|---|---|---|
| 5,281,420 A | * | 1/1994 | Kelm et al. | 424/452 |
| 2002/0137973 A1 | * | 9/2002 | Reeve et al. | 568/621 |
| 2003/0180363 A1 | * | 9/2003 | Seo et al. | 424/486 |
| 2006/0074027 A1 | | 4/2006 | Saito et al. | |
| 2006/0128673 A1 | | 6/2006 | Firnges et al. | |

FOREIGN PATENT DOCUMENTS

| | | |
|---|---|---|
| WO | WO 01/12155 A1 | 2/2001 |
| WO | WO 03/026647 A1 | 4/2003 |
| WO | WO 03/026648 A1 | 4/2003 |
| WO | WO 2005/041929 A1 | 5/2005 |
| WO | WO 2005/053612 A2 | 6/2005 |
| WO | WO 2005/053727 A2 | 6/2005 |
| WO | WO 2005/063206 A1 | 7/2005 |
| WO | 2006/045799 * | 5/2006 |
| WO | WO 2006/045799 A2 | 5/2006 |
| WO | WO 2006/113631 A2 | 10/2006 |
| WO | WO 2006/135480 A2 | 12/2006 |

OTHER PUBLICATIONS

Definition of embedded www.the freedictionary.com/embedded. Nov. 2010.*
Masayuki Yokoyama. Drug Targeting With Nano-Sized Carrier Systems. Jan. 17, 2005.* European Search Report of Application No. EP 06 12 2548, mailed Apr. 25, 2007.
International Search Report of PCT/EP2007/061194, mailed Jan. 10, 2008.
Vervaet, C., et al. "Continuous granulation in the pharmaceutical industry", Chem. Eng. Sci., vol. 60, 2005, pp. 3949-3957, XP002458753, the whole document.
Uchegbu et al., Polymers in Drug Delivery, CRC Press, May 2006, p. 112.

* cited by examiner

*Primary Examiner* — Shanon A Foley
*Assistant Examiner* — Sarah Al-Awadi
(74) *Attorney, Agent, or Firm* — Finnegan, Henderson, Farabow, Garrett & Dunner, L.L.P.

(57) ABSTRACT

The present invention relates to a thermostable solid composition containing nanosized micelles, the micelles containing a poorly soluble chemical substance, such as a biologically active substance, dissolved in an auxiliary material, and the micelles being embedded in a water soluble carrier. The invention further relates to a process for preparing a thermostable solid composition and to a process for preparing pharmaceutical dosage forms comprising the same.

22 Claims, 1 Drawing Sheet

EMBEDDED MICELLAR NANOPARTICLES

This application claims the benefit of priority of U.S. Provisional Application No. 60/853,023, filed on Oct. 20, 2006, the disclosure of which is incorporated herein by reference.

A large proportion of new drug molecules emerging from drug discovery programs are showing poor solubility in aqueous media or they are practically insoluble in aqueous media. Therefore, it is very challenging to formulate these active substances in a way that they can be administered parenterally or orally. The dissolution velocity and intestinal permeability are key determinants for the bioavailability, particularly for perorally administered drugs (low solubility in general is correlated with low dissolution velocity, law by Noyes-Whitney (Jinno et al., Effect of particle size reduction on dissolution and oral absorption of a poorly water-soluble drug, cilostazol, in beagle dogs, J. of Controlled Release 111 (1-2), 56-64, 2006). According to the Biopharmaceutics Classification System (G. L. Amidon, H. Lennernas, V. P. Shah, and J. R. Crison. A theoretical basis for a biopharmaceutics drug classification: the correlation of in vitro drug product dissolution and in vivo bioavailability. Pharm. Res. 12:413-420 (1995)), poorly soluble drugs belong either to BCS class II or BCS class IV. BCS class IV means the drug shows simultaneously poor solubility and low permeability, whereas the bioavailability of BCS class II drugs is typically dissolution rate limited (Formulation of poorly water-soluble drugs for oral administration: Physicochemical and physiological issues and the lipid formulation classification system, Colin W. Pouton, European Journal of Pharmaceutical Sciences 2006, 29, 278-87). That means that the bioavailability of BCS class II drugs can be increased by improving their dissolution velocity and/or the saturation solubility $c_s$.

Various formulation strategies have been applied to improve the solubility and dissolution rate of poorly soluble drugs.

The formation of inclusion complexes of active substances with cyclodextrines can improve the solubility of drugs (see e.g., WO9932107 disclosing the use of cyclodextrins for solubilization of THC). Cyclodextrines are cyclic oligomers of dextrose or dextrose derivatives, which can form a reversible, non-covalent association with poorly soluble drugs to solubilize them.

Lipid based systems, such as emulsions, microemulsions, self-emulsifying drug delivery systems (SEDDS) or self-microemulsifying drug delivery systems (SMEDDS) are suitable for active substances which are soluble in lipids and oils. In these lipid formulations, the active substance is dissolved in oils or lipids, which either forms an emulsion or forms an emulsion system upon dilution with water.

In situations where the active substance is kept in the solid form, one approach that has been applied for improving the dissolution behavior of poorly soluble drugs is particle size reduction of the solid amorphous or crystalline active substance to produce solid amorphous or crystalline material with decreased particle sizes. The decreased particle size leads to an increased surface area. Due to the greater surface area the drug particles have an improved dissolution velocity.

In general, in the production of materials with decreased particle sizes, distinction is made between top-down and bottom-up technologies. Top-down technologies involve an energy input to break down large particles to small particles. Depending on the employed technique, mean particle sizes of the substance to be milled can be obtained in the micrometer range (e.g., jet-milling, hammer milling) or in the nanometer range (e.g., wet ball milling and high pressure homogenization). For the latter, the use of a micronized starting material is recommended (see e.g., U.S. Pat. Nos. 5,145,684 and 5,858,410). A typical drawback of these technologies is that they require enormous amounts of energy to break down the starting material.

Bottom-up technologies are used to produce drug nanocrystals via precipitation. This technology is described in the old pharmacopeia as "via humida paratum." The active substance is dissolved in the solvent, the solvent is added to a non-solvent or anti-solvent (which is miscible with the solvent) and the active substance precipitates in the form of amorphous or crystalline nanoparticles, the latter are also referred to as drug nanocrystals. The particles are generally stabilized by surfactants or polymeric stabilizers. This principle was applied to produce so called "Hydrosols" (U.S. Pat. No. 5,389,382). Recently some modifications of this precipitation principle (U.S. Patent Publication No. 20050139144) were described. It is, however, very difficult to fix the precipitated crystals in the nanosize range. Nanoparticulate structures normally tend to grow to form microparticles or microcrystals. One approach to solve this problem is to immediately dry the prepared suspension, e.g., by lyphilization (Sucker, H., Hydrosole-eine Alternativefür die parenterale Anwendung von schwer wasserlöslichen Wirkstoffen, in: Müller, R. H., Hildebrand, G. E., (Hrsg.), Pharmazeutische Technologie: Moderne Arzneiformen, 2. Auflage, 1998, WVG, Stuttgart).

More recently, particle size reduction processes involving supercritical fluids or spray-freeze drying have been described in the literature for the production of solid drug nanoparticles (Jiahui Hu, Keith P. Johnston, and Robert O. Williams III, Nanoparticle Engineering Processes for Enhancing the Dissolution Rates of Poorly Water Soluble Drugs, DRUG DEVELOPMENT AND INDUSTRIAL PHARMACY, Vol. 30, No. 3, pp. 233-245, 2004).

All particle size reduction technologies have one common drawback; normally, the drug needs to be dissolved to be absorbed from the gut. For some very poorly soluble drugs the decrease of particle size might not be sufficient to improve the dissolution behavior and to increase the bioavailability.

Another approach to improve the dissolution behavior of poorly soluble active substances is the incorporation of these substances in amorphous systems, like solid dispersions. The term "solid dispersion" defines a system in a solid state (as opposed to a liquid or gaseous system) comprising at least two components, wherein one component is dispersed more or less evenly throughout the other component or components. A solid dispersion that is chemically and physically uniform or homogenous throughout or is made up of one phase as defined in thermodynamics can also be referred to as a solid solution (e.g., WO97/044014). The solid matrix can be either crystalline or amorphous. The drug can be dispersed molecularly or exist in amorphous particles (clusters) as well as crystalline particles (solid dispersion). Examples of such a solid dispersion are the tebufelone formulation described in U.S. Pat. No. 5,281,420, and the bioactive peptide formulation described in International Publication WO 2005/053727.

Solid dispersions can be prepared using various methods, e.g., the fusion method, the hot-melt extrusion, the solvent evaporation method or the supercritical fluid method (D. J. van Drooge "Combining the Incompatible", Rijksuniversiteit Groningen, PhD-Thesis 2006). Solid dispersions or solid solutions can comprise surfactants or other excipients to enhance the dissolution or to stabilize the drug. Several techniques for the production of solid dispersions are discussed in U.S. Patent Publication No. 20050266088A1. This publication also discloses a process to produce a sugar glass of a lipophilic compound where the lipophilic compound is dissolved in a co-solvent, preferably a $C_1$-$C_6$ alcohol. Typically the solvent has a high vapor pressure and a high melting point. However, because high vapor pressure is used, flammable co-solvents may cause difficulties in large scale production, especially when spray-drying is used as the drying technique. In order to protect the systems against explosion, the oxygen content in the drying air has to be reduced. Furthermore, the lipophilic compound is not sufficiently stabilized in the aqueous co-solvent system and tends to precipitate out. For that reason, a fast processing is suggested in order to avoid the occurrence of "clouding".

When the active substance is hydrophobic, but not lipophilic, i.e., not soluble in lipids and oils, co-solvents or co-solvent-surfactant mixtures can be used to solubilize the active substance. In order to classify the different solubilized systems C. Pouton has introduced a lipid formulation classification system (LFCS). A recent version of this scheme distinguishes four different formulation types (Formulation of poorly water-soluble drugs for oral administration: Physicochemical and physiological issues and the lipid formulation classification system, Colin W. Pouton, European Journal of Pharmaceutical Sciences 2006, 29, 278-87). LFCS type IV describes oil-free formulations based on surfactant-co-solvent mixtures. Normally, these surfactant-co-solvent mixtures are filled into soft gelatin capsules or sealed hard-gelatin capsules. When administered orally the drug is released after the dissolution of the capsule shell. Since the drug is already dissolved in the carrier, it can be absorbed quickly (Liquid-Filled and Seal Hard Gelatine Capsule Technologies, Ewart T. Cole, in: Modified-Release Drug Delivery Technology, eds. M. J. Rathbon, J. Hadgraft, M. S. Roberts, Marcel Dekker, Basel, 2003).

In order to produce a conventional solid dosage form from a poorly soluble liquid drug, the production of "powdered solutions" was suggested by Spireas et al. (Spireas et al., Powdered solution technology: principles and mechanisms, Pharm. Res. 9 No. 10, 1351-1358, 1992). The "powdered solution" was produced by admixing the liquid drugs or drug solutions with a selected carrier. The product obtained by this technology is a physical mixture or blend of a drug/surfactant solution and the selected carrier. Examples of these kind of formulations are disclosed in WO 2005/041929, WO 2006/113631 and WO 2006/135480. However, typical drawbacks of the resulting powder is its poor flowability, its poor thermostability, and/or its poor compressability.

It is an objective of the present invention to provide further improved formulations for compounds, especially biologically active compounds, that can be prepared using commercially available materials and standard processes and equipment. In the case of biologically active compounds a further aim of the present invention is to provide formulations with good bioavailability.

The present invention relates to a thermostable composition having improved dissolution behavior, the composition comprising nanosized micelles, wherein the micelles comprise a poorly soluble compound. In one embodiment, the pharmaceutical composition of the present invention comprises nanosized micelles, wherein the micelles comprise a surfactant or a surfactant-co-solvent mixture containing a poorly soluble chemical substance, such as a poorly soluble drug, wherein the micelles are embedded in a water-soluble matrix of a water-soluble carrier, such as a pharmaceutically acceptable carrier.

Another aspect of the invention relates to the preparation of a pharmaceutical composition comprising, preparing an aqueous micellar solution comprising a poorly soluble compound, an auxiliary material or a mixture of auxiliary materials, and a water-soluble matrix, and drying the micellar solution to embed these micelles in the water-soluble matrix to obtain a thermostable composition. Micelles containing the poorly soluble compound are produced using one or more surfactants and optionally one or more co-solvents.

DESCRIPTION OF THE INVENTION

Figure 1:
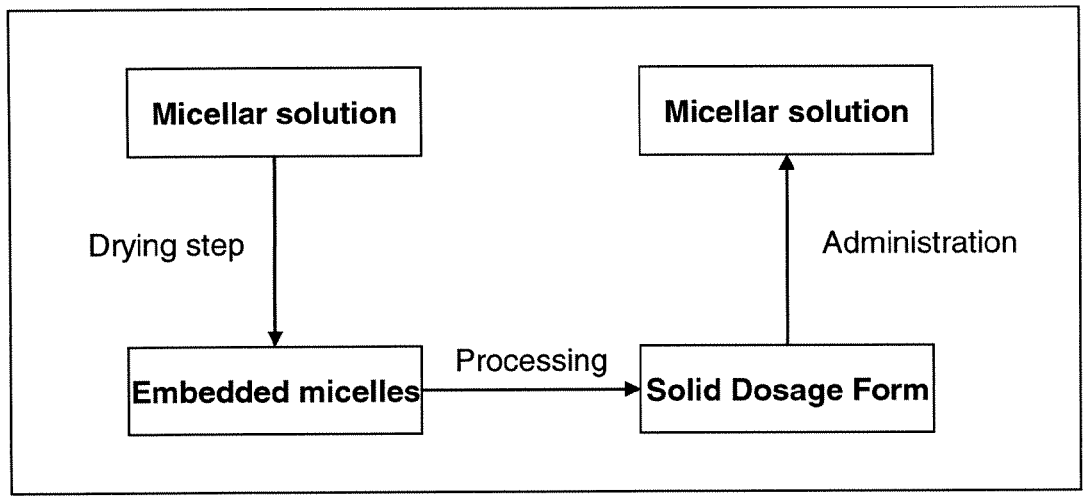
FIG. 1 is a diagram of the general process of preparing a composition, for example a pharmaceutical composition, according to the present invention.

In a first aspect, the present invention relates to a thermostable solid composition comprising nanosized micelles, wherein said micelles comprise a poorly soluble chemical substance dissolved in an auxiliary material, and wherein said micelles are embedded in a water-soluble carrier.

In another aspect, the present invention relates to a thermostable solid pharmaceutical composition comprising nanosized micelles, wherein said micelles comprise a poorly soluble biologically active substance dissolved in an auxiliary material, and wherein said micelles are embedded in a matrix of a water soluble pharmaceutically acceptable carrier.

In the framework of the present invention the term thermostable means that the formulation remains a free flowing stable powder when heated above the melting point of the main auxiliary material. This means that the formulation remains physically stable when heated 5°, 10°, 20°, 30°, 40° or 50° C. above the melting point of the main auxiliary material.

For example, Vitamin E TPGS (d-alpha-tocopheryl polyethylene glycol 1000 succinate) has a melting point of 36° C. (Reference: Eastman, Material Safety Data Sheet of Vit E TPGS NF Grade). A person skilled in the art would assume that if Vitamin E TPGS is the main component of a formulation, this formulation would at least experience partial melting when exposed to a temperature much above 36° C., for instance 80° C. However, if Vitamin E TPGS is used as an auxiliary material in the present invention, the Vitamin E TPGS forms micelles, and the micelles of Vitamin E TPGS (and an active substance) are embedded in a water-soluble matrix material, which has a melting point above 36° C. Thus, the resulting powder will not show a major change in powder morphology and flowability. It remains a stable, free-flowing powder even if exposed to temperatures 5°, 10°, 20°, 30°, 40° or 50° C. above the melting point of the main auxiliary material, Vitamin E TPGS.

In the framework of the present invention the terms biologically active substance, pharmaceutically active substance, drug, active compound, active ingredient are used interchangeably to refer to a chemical substance or chemical compound which, when administered to a human or animal being, induces a pharmacological effect.

The term poorly soluble compound in the framework of the present invention means a compound which has a solubility in water at 37° C. of less than 33 g/L. In particular for pharmaceutically active compounds, the term poorly soluble compound is used to describe a compound that has a solubility of less than 33 g/L under the conditions, in particular the pH, at the site in vivo (e.g., in the stomach, in the intestines, subcutaneous) where the compound is intended to become available to the body (in particular where the compound is dissolved to be absorbed by the body). Thus, for example a poorly soluble compound intended to dissolve in the stomach, has a solubility below 33 g/l in gastric fluid (pH of about 1-3) and a poorly soluble compound to be dissolved in the intestines has a solubility below 33 g/l in intestinal fluid (typically up to about pH 7.4). (Ref. US 0050266088, Frijlink). The present invention is especially useful for even more poorly soluble compounds, such as compounds having a solubility in the gastrointestinal fluid of below 10 g/L, 4 g/L, 1 g/L, 100 mg/L, 40 mg/L, 10 mg/L, 4 mg/L, 1 mg/L, 0.4 mg/L or 0.1 mg/L.

The poorly soluble compounds that can be processed according to this invention can be liquid, semi-solid, solid amorphous, liquid crystalline or solid crystalline.

The poorly soluble compounds to be processed according to this invention can be pharmaceutically active agents and can be chosen from analgesics, anti-arrhythmic agents, anti-asthma agents, anti-biotic agents, anti-helminthics, anti-inflammatory agents, anti-viral agents, anti-coagulants, anti-depressants, anti-diabetics, anti-epileptics, anti-erectile dysfunction agents, anti-fungal agents, anti-gout agents, anti-hypertensive agents, anti-malarials, anti-migraine agents, anti-muscarinic agents, anti-neoplastic agents, anti-obesity agents, anti-parkinsonian agents, anti-protozoal agents, anti-thyroid agents, anti-tussives, anxiolytics, beta-blockers, hypnotics, immunosuppressants, neuroleptics, cannabinoid receptor agonists and antagonists, cardic inotropic agents, cell adhesion inhibitors, corticosteroids, cytokine receptor activity modulators, diuretics, gastro-intestinal agents, histamine H-receptor antagonists, keratolytics, lipid regulating agents, muscle relaxants, nitrates and other anti-anginal agents, non-steroid anti-asthma agents, opioid analgesics, sedatives, sex hormones and stimulants.

Some examples of poorly soluble compounds are poorly soluble cannabinoid agonists, inverse agonists and antagonists. Some examples of these compounds are the compounds disclosed in WO01/70700, WO02/076949, WO03/026647, WO03/026648, WO03/027076, WO2005/074920, WO 2005/080345, WO 20.05/118553 and WO2006/087355 such as (4S)-3-(4-chlorophenyl)-4,5-dihydro-N-methyl-4-phenyl-N'-(1-piperidinyl-sulfonyl)-1H-pyrazole-1-carboximidamide described in WO 03/026648 and (4S)-3-(4-chlorophenyl)-N-[(4-chlorophenyl)sulfonyl]-4,5-dihydro-N'-methyl-4-phenyl-1H-pyrazole-1-carboximidamide (also known as ibipinabant or SLV319) and (4S)-3-(4-chlorophenyl)-4,5-dihydro-N-methyl-4-phenyl-N'-[[4-(trifluoromethyl)phenyl]sulfonyl]-1H-pyrazole-1-carboximidamide as described in WO 02/076949.

The poorly soluble compound in the composition of the present invention typically has a log P lower than 10, for example lower than 5, or lower than 2.5. The poorly soluble compound in the composition may be present in an amount from 0.05% w/w to at least 50% w/w, for example in an amount from 0.05 to 10% w/w, or from 0.05% to 5% w/w, or from 0.05% to 1% w/w, based on the total weight of the composition.

The term auxiliary material in the framework of the present invention is a material that enables the formation of micelles when it is brought in contact with water or a material that has a positive effect on the stability of micelles when they have been formed, such as a surfactant, a co-solvent, or a mixture of a surfactant and a co-solvent.

The term micelle in the framework of the present invention means an association of surfactant molecules, which in aqueous solutions are above the Krafft point and the critical micellization concentration (Ref. Römpp Online Dictionary).

According to the IUPAC, surfactants in solution often form association colloids. That is, they tend to form aggregates of colloidal dimensions, which exist in equilibrium with the molecules or ions from which they are formed. Such aggregates are termed micelles.

Krafft point means the temperature (more precisely, narrow temperature range) above which the solubility of a surfactant in water rises sharply. At this temperature the solubility of the surfactant becomes equal to the critical micelle concentration. It can be determined by locating the abrupt change in slope of a graph of the logarithm of the solubility against t or 1/T. There is a relatively small range of surfactant concentrations separating the limit below which virtually no micelles are detected and the limit above which virtually all additional surfactant molecules form micelles. Many properties of surfactant solutions, if plotted against the concentration, appear to change at a different rate above and below this range. By extrapolating the loci of such a property above and below this range until they intersect, a value may be obtained known as the critical micellization concentration (critical micelle concentration) (IUPAC Compendium of Chemical Terminology, Goldbook).

The micelles in the composition according to the present invention have a mean size smaller than 1000 nm, for example smaller than 500 nm, or smaller than 200 nm, or smaller than 100 nm.

The term mean size in the framework of the present invention refers to an effective average diameter determined by dynamic light scattering methods (e.g., photocorrelation spectroscopy (PCS), laser diffraction (LD), low-angle laser light scattering (LALLS), medium-angle laser light scattering (MALLS), light obscuration methods (Coulter method, for example), rheology, or microscopy (light or electron) within the ranges set forth above). By "an effective average particle size of less than about x nm" it is meant that at least 90% of the particles have a weight average particle size of less than about x nm when measured by the above-noted techniques.

The composition according to the present invention may comprise at least 10% of a surfactant, or at least 30%, or at least 50%, and may comprise up to 99.95% of surfactant. Optionally the composition contains also one or more co-solvents and/or one or more co-surfactants.

In one embodiment, the pharmaceutical composition of the present invention comprises a surfactant and an optional co-surfactant such as those listed in M. M. Rieger, "Surfactants", Chapter 8 in Pharmaceutical Dosage Forms, Marcel Dekker Inc., (1993), p. 285-359. For example, surfactants that are useful in the present invention are surfactants with a HLB value larger than 8. Some examples of surfactants are polyoxyethylene stearates (such as Solutol®), Polyoxyethylene sorbitan fatty acid esters (such as Tween®), Polyoxyethylen Castor Oil Derivatives (such as Chremophor®), Vitamin E TPGS, nonionic polyoxyethylene-polyoxypropylene block co-polymers (such as Poloxamer®), water-soluble long chain organic phosphate esters (such as Arlatone®), and inulin lauryl carbamate (such as Inutec SP1®).

In one embodiment, the optional co-solvent used in the pharmaceutical composition is a pharmaceutically acceptable non-volatile co-solvent, which is a substance having a vapor pressure lower than 0.50 mm Hg at 25° C. The pharmaceutical composition of the present invention relates to solubilizing mixtures of type IV of the lipid formulation classification system (LFCS), defined by Pouton (see paragraph [0012]) as oil-free formulations based on surfactants and co-solvents. Therefore, oils are specifically excluded as co-solvents in the present invention. LFCS Type I formulations (Non-disperging; requireg digestion), LFCS Type II formulations (SEDDS without water-soluble components), LFCS Type IIIA formulations (SEDDS/SMEDDS with water soluble components), and LFCS Type IIIB formulations (SMEDDS with water soluble components and low oil content) are also excluded.

Examples of a nonvolatile co-solvent include, without limitation, alkylene glycols such as, polyethylene glycol (PEG), propylene glycol, diethylene glycol monoethyl ether, glyceryl triacetate, benzyl alcohol, polyhydric alcohols, e.g., mannitol, sorbitol and xylitol; polyoxyethylenes; linear polyols, e.g., ethylene glycol, 1,6-hexanediol, neopentyl glycol and methoxypolyethylene glycol; and mixtures thereof.

Particularly useful as a nonvolatile co-solvent in the present invention is PEG, which is a polymer of ethylene oxide that conforms generally to the formula $(HOCH_2CH_2)_n$ OH wherein n is the number of units, which is also the number defining the average molecular weight (m.w.) of the polymer.

The types of PEG useful in the present invention can be categorized by its state of matter, i.e., whether the substance exists in a solid or liquid form at room temperature and pressure. In the framework of the present invention, "liquid PEG" refers to PEG having a molecular weight (m.w.) such that the substance is in a liquid state at room temperature and pressure. For example, PEG with an average m.w. less than 800 Daltons. Particularly useful are PEG 400 (m.w. from about 380-420 Daltons), PEG 600 (m.w. from about 570-630 Daltons), and mixtures thereof. PEGs are commercially-available from Dow Chemical (Danbury, Conn.) under the CARBOWAX SENTRY line of products.

In the framework of the present invention, "solid PEG" refers to PEG having a molecular weight such that the substance is in a solid state at room temperature and pressure. For example, PEG having an average m.w. ranging from 900 to 20,000 Daltons is a solid PEG. Particularly useful solid PEGs are those having a m.w. from 3,350 Daltons (m.w. from about 3015 to about 3685 Daltons) to 8,000 Daltons (m.w. from about 7,000 to 9,000 Daltons). Especially useful as a solid PEG are PEG 3350, PEG 4000 (m.w. from about 3,600 to 4,400 Daltons), PEG 8000, and mixtures thereof.

When replacing a liquid PEG (e.g., PEG 400) with a solid PEG (e.g., PEG 4000), the resulting drug-surfactant-co-solvent mixture has to be heated to 80° C. It has surprisingly been found that the release behavior is not changed much when PEG 400 is replaced by PEG 4000, although the cake resulting from freeze drying of a PEG 4000 product is more rigid than when PEG 400 is used.

When present, the formulation comprises the co-solvent in an amount of from 0.01% w/w to 99.95% w/w, for example from 10.0% w/w to 90.0% w/w, and further for example from 20.0% w/w to 70.0% w/w.

The water soluble carrier (also indicated as matrix) can be any polymeric material that is soluble in water. A matrix material can be considered being soluble in water if at least one part of the matrix material can be dissolved in 10 to 30 parts water (definition according to USP 24, page 2254).

For pharmaceutical compositions the water soluble carrier should be pharmaceutically acceptable. Examples of pharmaceutically acceptable carrier that are useful in the present invention are chosen from:

alkylcelluloses such as methylcellulose;
hydroxyalkylcelluloses such as hydroxymethylcellulese, hydroxyethylcellulose, hydroxypropylcellulose and hydroxybutylcellulose;
hydroxyalkyl alkylcelluloses such as hydroxyethyl methylcellulose and hydroxypropyl-methylcellulose;
carboxyalkylcelluloses such as carboxymethylcellulose;
alkali metal salts of carboxyalkylcelluloses such as sodium carboxymethylcellulose;
carboxyalkylalkylcelluloses such as carboxymethylethylcellulose;
carboxyalkylcellulose esters;
starches;
pectines such as sodium carboxymethylamylopectine;
chitin derivates such as chitosan;
polysaccharides such as alginic acid, alkali metal and ammonium salts thereof,
carrageenans, galactomannans, tragacanth, agar-agar, gummi arabicum, guar gummi and xanthan gummi;
polyacrylic acids and the salts thereof;
polymethacrylic acids and the salts thereof, methacrylate copolymers;
polyvinylalcohol;
polyvinylpyrrolidone, copolymers of polyvinylpyrrolidone with vinyl acetate;
polyalkylene oxides such as polyethylene oxide and polypropylene oxide and copolymers of ethylene oxide and propylene oxide.

Non-enumerated polymers which are pharmaceutically acceptable and have appropriate physico-chemical properties as defined hereinbefore are equally suited as a carrier in the present invention for pharmaceutical compositions.

Examples of water-soluble polymers that are useful in the present invention include hydroxypropyl methylcelluloses and HPMC. HPMC contains sufficient hydroxypropyl and methoxy groups to render it water-soluble. HPMC's having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule. Hypromellose is the United States Adopted Name for hydroxypropylmethylcellulose.

The composition according to the present invention may include one or more other additives. In the case of a pharmaceutical composition these additives should be pharmaceutically acceptable additives such as flavouring agents, colourants, binders, fillers, filler-binders, lubricants, disintegration aids and/or other pharmaceutically acceptable additives.

The preparation of a composition according to the present invention involves the preparation of an aqueous micellar solution of a poorly soluble compound followed by a drying step to embed these micelles in a water-soluble matrix of a carrier, such as a pharmaceutically acceptable carrier. Micelles containing the poorly soluble compound are produced by using one or more surfactants. If desired, one or more co-solvents can be also included.

In another aspect of the invention the micellar solution comprising the poorly soluble compound is prepared by dissolving the poorly soluble compound in one or more surfactants. Dissolving means that the poorly soluble compound is substantially mono-molecularly dispersed, i.e., at least 95%, at least 98%, at least 99%, at least 99.5%, or at least 99.9% of the poorly soluble compound is mono-molecularly dispersed. If necessary, one or more co-solvents can be added. In one aspect of the invention, energy can be applied to enable the complete molecular distribution by heating, blending, or mixing of the components. When the components have formed a molecular dispersed system they are mixed together with the aqueous phase to form a micellar solution. The aqueous phase can contain a dissolved matrix of a carrier, such as a pharmaceutically acceptable carrier, or the water-soluble matrix of the carrier is dissolved afterwards in the micellar solution. This mixture is dried to obtain a solid powder. The powder can be used as it is or mixed with other excipients and processed further.

In another aspect of the invention, the composition according to the invention facilitates the absorption of poorly soluble drugs by forming micellar solutions of the drug when the composition is administered.

A further aspect of the invention is that the composition, for example the solid powder, can be easily processed into formulations for capsule filling, even using excipients which are known to be not compatible with hard gelatin capsules (e.g., PEG 400, Glycerol, Polyoxyl 35 Castor Oil (e.g., Cremophor EL®), Propylene Glycol, Diethylene glycol monoethyl ether (e.g., Transcutol P®), Sorbitan monooleate (e.g., Span 80®)).

Freeze drying is typically not the production process used for large scale production and is normally only applied for extreme labile drugs, such as proteins. Spray drying is more convenient and better suitable for large scale production. Therefore, spray-drying was tested as the drying method for the micellar solutions according to the invention and was found to be very suitable for the production. Since no flammable co-solvents with high vapor pressure are used, the production of the spray dried powders can be performed on standard equipment without special protection against explosion. Furthermore, the micellar solutions are stable for hours, in some cases even for days, without precipitation of the drug. The dissolution testing has shown that approximately the same dissolution velocity can be obtained, irrespectively of the utilized drying method.

Particle size analysis using laser diffraction was performed in order to test the influence of the drying step on the particle size of the micelles and it was shown that the particle size before spray-drying and after redispersion from the spray-dried powder was in the same order of magnitude. From this result it can be concluded that the drying process does not change the size of the resulting micelles.

The inventive method is not limited to surfactant-co-solvent mixtures. Once an aqueous micellar solution of the poorly soluble compound can be obtained in the presence of a dissolved pharmaceutically acceptable carrier, the resulting micellar solution can be processed according to the invention.

A pharmaceutical composition according to the present invention may be processed further into any solid dosage form for any route of administration. Dosage forms of particular interest are granules, compressed (immediate release) tablets for oral delivery, sublingual or buccal tablets, and powder or granular filled hard gelatin capsules or sachets.

A tablet is a common type of solid dosage form used to administer a pharmaceutical composition in the pharmaceutical industry. However, so far it is difficult to produce tablets from liquid or semisolid formulations, which contain the poorly soluble drug in solubilized (i.e., dissolved) form. One procedure that has been used to produce such tablets is the adsorption of liquid drugs or drug solution onto selected carriers (Spireas et al., Powdered solution technology: principles and mechanisms, Pharm. Res. 9 No. 10, 1351-1358, 1992). However, a typical drawback of the resulting powder is its poor flowability and compressability. It is an objective of this invention to provide a solution for this problem. The powders produced according to the present invention, in particular the powders produced by spray drying, show very good flowability. The dry powder can be mixed in dry state with pharmaceutical excipients. The resulting powder mixtures can be filled directly into capsules, however, even a compression to tablets is possible. The tablets obtained have shown a very fast drug release, the release velocity was comparable to that of the capsule formulation of the similar composed powder. When granulated fumed-silica (e.g., AEROPERL® 300) was used as a filler in the present invention, a very fast disintegration of the tablets and therefore, a good drug release was obtained.

Tablets produced according to the present invention have shown a much better drug release then with those produced by standard approaches (e.g, melt-extrusion or liquid filled capsules).

When comparing the release profile of the tablet formulation produced according to the present invention with a formulation prepared by melt-extrusion, it appeared that it was very difficult to powder the solidified mass obtained by melt-extrusion; therefore, only inhomogeneous tablets could be obtained and only 60% of the drug was released after 20 minutes compared with a release of more than 80% when the formulation according to the present invention was used.

The production of liquid-filled capsules is another state of the art technology to provide a dosage form that can be used for administering a pharmaceutical composition. When a molten drug-surfactant-co-solvent (PEG 4000) mixture was filled into hard gelatin capsules, solidified, and submitted for drug release studies, it appeared that the molten drug-surfactant-co-solvent mixture was compatible with the capsule shell. However, these capsules have also shown a relatively slow drug release. After 20 minutes only 52% of the drug was released. Thus, drug release from a formulation according to the present invention, which has a release of more than 80% is superior as compared to drug release from conventional liquid-filled capsules known in the art.

Although freeze drying is not typically used for large scale production, it can be used according to the present invention for the production of powders that can be compressed into tablets. Freeze drying may be used when only a limited amount of drug is available (e.g., in early development stages), and tablets according the present invention are desired. It was found that the freeze dried powder could be successfully compressed into tablets, even without adding any additional excipient. These "unformulated" tablets have shown a promising drug release of approx. 62% after 20 minutes, which can certainly be raised by adding standard tabletting excipients.

The present invention also relates to a process for preparing the composition of the present invention.

In a first aspect, the invention relates to a process for preparing a solid pharmaceutical composition as described above, comprising the following steps:
  a) dissolving a poorly soluble active substance in an auxiliary material or a mixture of auxiliary materials;
  b) optionally adding one or more additional auxiliary materials to the solution obtained in (a);
  c) mixing the solution obtained in (a) or (b) with water to form nanosized micelles;
  d) dissolving a matrix forming material in the mixture obtained in (c); and
  e) drying the mixture obtained in (d) to obtain a solid pharmaceutical composition, wherein the micelles are embedded in the matrix forming material.

In a further aspect the invention relates to a process for preparing a solid pharmaceutical composition as described above, comprising the following steps:
  a) dissolving a poorly soluble active substance in an auxiliary material or a mixture of auxiliary materials;
  b) optionally adding one or more additional auxiliary materials to the solution obtained in (a);
  c) dissolving a matrix forming material in water;

d) mixing the solution obtained in (a) or (b) with the solution obtained in (c) to form nanosized micelles; and e) drying the mixture obtained in (d) to obtain a solid pharmaceutical composition, wherein the micelles are embedded in the matrix forming material.

In a further aspect the invention relates to a process for preparing a solid pharmaceutical composition as described above, comprising the following steps:

a) dissolving a poorly soluble active substance in either an auxiliary material or a mixture of auxiliary materials;

b) dissolving the solution obtained in (a) in water to form nanosized micelles;

c) optionally adding one or more additional auxiliary materials to the solution obtained in (b);

d) dissolving a matrix forming material in the solution obtained in (b) or (c); and e) drying the mixture obtained in (d) to obtain a solid pharmaceutical composition, wherein the micelles are embedded in the matrix forming material.

In another aspect the invention relates to a process of preparing a solid pharmaceutical composition as described above, comprising the following steps:

a) dissolving an auxiliary material or a mixture of auxiliary materials in water;

b) dissolving a poorly soluble active substance in the solution obtained in (a);

c) optionally adding one or more additional auxiliary materials to the solution obtained in (b), wherein the solution obtained in (b) or (c) contains micelles comprising the poorly soluble active substance;

d) dissolving a matrix forming material in the solution containing the micelles comprising the poorly soluble active substance obtained in (b) or (c); and e) drying the mixture obtained in (d) to obtain a solid pharmaceutical composition, wherein the micelles are embedded in the matrix forming material.

When applying the processes discussed above, the micelles can be formed in either step (a), step (b), step (c) or step (d). For example, micelles can be formed in step (a) when the auxiliary material or mixture of auxiliary materials used in step (a) contains a surfactant and the surfactant is brought into contact with water in step (a). In that case, the micelles do not yet contain the poorly soluble active substance and the poorly soluble active substance is included in the micelles in step (b). Alternatively the micelles can be formed in step (b) when the surfactant is brought into contact with water in step (b). As a third alternative, the micelles are formed in step (c), when they have not yet been formed in step (a) or (b). In this case, the surfactant is added for the first time in step (c) and/or the surfactant is brought into contact with water in step (c). As a fourth alternative, the micelles are formed in step (d), when the surfactant is first brought into contact with water in step (d).

In yet another aspect, the invention relates to a process for preparing a solid pharmaceutical composition as described above, comprising the following steps:

A) combining a poorly soluble active substance, an auxiliary material or a mixture of auxiliary materials, optionally one or more additional auxiliary materials, a matrix forming material, and water to form nanosized micelles; and B) drying the mixture obtained in (A) to obtain a solid pharmaceutical composition, wherein the micelles are embedded in the matrix forming material.

The drying step indicated above can be performed by freeze drying, spray drying or freeze spray drying. Spray drying is commonly used.

The powder formed by applying one of the processes described above is free-flowing and remains stable and free-flowing when heated above the melting temperature of the main auxiliary material, even when the amount of matrix forming material is very low, such as lower than 50%, even lower than 30%, even lower than 20% or even lower than 10%. In the powder, the micelles remain existent as in the original aqueous micellar solution, but they are now embedded in the solid matrix and thereby stabilized. Upon dissolution in water the original aqueous micellar solution is formed again (see FIG. 1).

The product after drying may be further processed into granules, compressed tablets, sublingual or buccal tablets or the dried composition may be filled into capsules or sachets in the form of a powder or in the form of granules with the aid of conventional methods and apparatuses.

It is an object of the present invention to obtain a thermostable solid composition comprising a poorly soluble active compound that has a very high bio-availability. A bio-availability study (in male beagle dogs) of formulations comprising a poorly soluble active compound, COMPOUND 1 (SLV330), was conducted. It was found that the relative bio-availability in male beagle dogs of the composition according to the present invention was about 6 times higher as compared with the relative bio-availability of a composition comprising micronized active compound (see Table 2 below).

Although the present invention is developed on the basis of active substances that can be used in the field of medicine, the principle can be used in other fields of technology wherein nanosized particles have an advantage. Therefore, the present invention is not restricted in its use to the field of medicine.

The following examples are only intended to further illustrate the invention in more detail, and therefore, these examples provided herein are not deemed to restrict the scope of the invention in any way.

EXAMPLES

Example 1

Materials and Methods

Materials: Polyethylene glycol (e.g., PEG 400 and PEG 4000), Polyoxyethylensorbitanmonooleat (e.g., Polysorbat 80®), Macrogol-15 hydroxystearate (e.g., Solutol® HS 15), anhydrous citric acid, mannitol, hydroxypropylmethylcellulose (e.g., HPMC E5®), d-alpha-tocopheryl polyethylene glycol 1000 (Vitamin E TPGS), sodium dodecyl sulfate (SDS), Polyvinylpolypyrrolidone (PVP-CL), Sodium Stearyl Fumarate (e.g., Pruv®), Microcrystalline cellulose (MCC) and granulated fumed silica (e.g., Aeropearl 300®) were obtained from commercial sources.

COMPOUND 1: (4S)-3-(4-chlorophenyl)-4,5-dihydro-N-methyl-4-phenyl-N'-(1-piperidinyl-sulfonyl)-1H-pyrazole-1-carboximidamide was prepared as described in WO 03/026648.

COMPOUND 2: (4S)-3-(4-chlorophenyl)-N-[(4-chlorophenyl)sulfonyl]-4,5-dihydro-N'-methyl-4-phenyl-1H-pyrazole-1-carboximidamide was prepared as described in WO 02/076949.

COMPOUND 3: (4S)-3-(4-chlorophenyl)-4,5-dihydro-N-methyl-4-phenyl-N'-[[4-(trifluoro-methyl)phenyl]sulfonyl]-1H-pyrazole-1-carboximidamide was prepared as described in WO 02/076949.

Methods

Plasma samples were analyzed according to the following procedure. Internal standard (20 µL, 250 ng/mL) was added to thawed plasma samples (20 µL). The samples were then subjected to protein precipitation using methanol (210 µL). The samples were mixed, centrifuged (5 minutes, 3400 rpm, room temperature) and 50 µL of the resulting supernatant was transferred into a 96-well plate. Formic acid (0.2%, 150 µL) was added to each well. The extracts were mixed and centrifuged (5 minutes, 3400 rpm, nominal 4° C.) before being submitted for LC-MS/MS analysis on a Waters Acquity HPLC connected to a Applied Biosystems API 4000. The mass spectrometer operation mode was Turbo IonSpray positive, the analytical column was a Waters Acquity BEH phenyl 1.7 um, 100 mm×2.1 mm (id). Concentrations of COMPOUND1 in calibration standards and QC samples were determined using a quadratic regression with the reciprocal of the concentration (1/x) as weighting. The data was collected and processed using Applied Biosystems/MDS Sciex Analyst™ software 1.4.1.

Example 2

Preparation of COMPOUND 1 Formulation (FD PEG 400)

50 mg of the poorly soluble drug COMPOUND 1 was weighed in a glass injection vial. Afterwards 950 mg of a surfactant-co-solvent mixture containing 66.34% (w/w) PEG 400, 16.58% (w/w) Polysorbat 80, 16.58% (w/w) Solutol® HS 15, and 0.5% anhydrous citric acid (w/w) was added to this vial. After complete dissolution of the drug, 4 ml of an aqueous Mannitol solution (10% w/w) was added to the vial and the contents were mixed well. Within the next 5 seconds the vial was put into a bath of liquid nitrogen to freeze the mixture rapidly. Finally, the frozen mixture was lyophilized in a lab freeze dryer (Christ Alpha 2-4, Salm and Kipp, The Netherlands) at −80° C. and 0.050 mbar for 48 hours. A fluffy cake was obtained.

Example 3

Preparation of COMPOUND 1 Formulation (FD PEG 4000)

50 mg of a poorly soluble drug (COMPOUND 1) was weighed in a glass injection vial. Afterwards 950 mg of a surfactant-co-solvent mixture containing 66.34% (w/w) PEG 4000, 16.58% (w/w) Polysorbat 80, 16.58% (w/w) Solutol® HS 15, and 0.5% anhydrous citric acid (w/w) was added to this vial. This mixture was stored in an oven at 80° C. until the drug was completely dissolved. Afterwards 4 ml of a heated (80° C.) aqueous Mannitol solution (10% w/w) was added to the vial and the contents were mixed well until any solid content was dissolved. Within the next 5 seconds the vial was put into a bath of liquid nitrogen to freeze the mixture rapidly. Finally, the frozen mixture was lyophilized in a lab freeze dryer (Christ Alpha 2-4, Salm and Kipp, The Netherlands) at −80° C. and 0.050 mbar for 48 hours. A cake was obtained that could be easily powdered with a spatula.

Example 4

Preparation of COMPOUND 1 Formulation (SD PEG 4000)

13.7 g of a poorly soluble drug (COMPOUND 1) was weighed in a glass flask. Afterwards 260 g of a surfactant-co-solvent mixture containing 66.34% (w/w) PEG 4000, 16.58% (w/w) Polysorbat 80, 16.58% (w/w) Solutol® HS 15, and 0.5% anhydrous citric acid (w/w) was added to this flask. This mixture was stored in an oven at 80° C. until the drug was completely dissolved. 1 g of this molten solution was mixed with 250 ml of an aqueous hydroxypropyl methylcellulose solution (HPMC Grad E5, 0.016% w/w). The resulting solution was then spray-dried using a Mini Spray Dryer Büchi 191 (Büchi, Switzerland). The airflow was 600 l/h, the inlet temperature was 150° C., the aspirator was set to 80%, the feed flow rate was about 5.5 g/min, and the outlet temperature under these conditions was about 90° C. A free-flowable powder was obtained.

Example 5

Preparation of COMPOUND 1 Formulation (SD TPGS)

1.0 g of a poorly soluble drug (COMPOUND 1) was weighed in a flask. Afterwards 20.0 g of a heated (80° C.) Vitamin E TPGS containing 0.5% (w/w) anhydrous citric acid was added to this flask. This mixture was stored in an oven at 80° C. until the drug was completely dissolved. 1 g of this molten solution was mixed with 25 ml of an aqueous hydroxypropyl methylcellulose solution (HPMC Grad E5, 0.16% w/w). The resulting solution was then spray-dried using an Mini Spray Dryer Büchi 191 (Büchi, Switzerland). The airflow was 600 l/h, the inlet temperature was 150° C., the aspirator was set to 80%, the feed flow rate was about 5.5 g/min, and the outlet temperature under these conditions was about 90° C. A free-flowable powder was obtained. This Example shows that the present invention is not limited to surfactant-co-solvent mixtures. Once an aqueous micellar solution of the poorly soluble compound was obtained in the presence of a dissolved pharmaceutically acceptable carrier, the resulting micellar solution was processed according to the present invention.

Example 6

Particle size COMPOUND 1 Formulation (before and after SD PEG 4000)

The particle size of the drug micelles was determined before and after spray drying using a laser diffractometer Coulter LS 13 320 (Beckman Coulter, Fullerton, Calif., USA) equipped with a Coulter Aqueous Liquid Module. The real refractive index for the fluid was set at 1.33 (water). For the sample the real refractive index was set at 1.46 and the imaginary refractive index at 0.01. 50 mg of a poorly soluble drug (COMPOUND 1) was weighed in a glass injection vial. Afterwards 950 mg of a heated (80° C.) surfactant-co-solvent mixture containing 66.67% (w/w) PEG 4000, 16.67% (w/w) Polysorbat 80, and 16.67% (w/w) Solutol® HS 15 was added to this vial. This mixture was stored in an oven at 80° C. until the drug was completely dissolved. 1 g of this molten solution was mixed with 250 ml of an aqueous hydroxypropyl methylcellulose solution (HPMC Grad E5, 0.016% w/w). The particle size of the resulting micellar solution determined as volume weighted diameter d 95% by laser diffraction was 345 nm. 1.4 g of a drug containing powder (containing 50 mg COMPOUND 1) produced according example 3 was dissolved in 250 mL water. The particle size of the resulting micellar solution determined as volume weighted diameter d 95% by laser diffraction was 254 nm.

Example 7

Tabletting of the FD Powder of COMPOUND 1

The powder resulting from Example 3 was compressed to a bifacial tablet with a diameter of 12.5 mm by using an experimental hydraulic press and a compaction pressure of 100 bars applied for 40 sec.

Example 8

Tabletting of the SD Powder of COMPOUND 1

325 mg of the powder produced according to Example 4 was mixed with 325 mg granulated hydrophilic fumed silica (AEROPERL® 300/30, Degussa AG, Germany), and 125 mg polyvinylpyrrolidone (Kollidon® CL, BASF, Germany). Then, the mixture was compressed to a bifacial tablet with a diameter of 12.5 mm by using an experimental hydraulic press and a compaction pressure of 40 bars applied for 2 sec.

Example 9

Release Profile PEG 400 Capsules (FD) of COMPOUND 1

The powder produced according to Example 2 was filled into hard gelatine capsules. The drug content in one capsule was 25 mg. The dissolution test was performed according USP II. The vessels were filled with 900 mL of 0.1 M HCl containing 0.5% w/v sodium dodecyl sulfate at 37.5° C. The paddle speed was set at 50 rpm during the first 90 minutes, after which the paddle speed was increased to 150 rpm for another 30 minutes. Samples of 10 mL were taken after 0, 5, 10, 20, 30, 45, 60, 90 and 120 minutes, filtered through a 0.22 µm filter. All experiments were performed in triplicate and the mean of these three experiments±the covariance was plotted as function of the time. Drug content in the samples was determined with HPLC. After 20 min. approx. 95% of the drug was released.

Example 10

Release Profile PEG 4000 Capsules (FD) of COMPOUND 1

The powder resulting from Example 3 was filled into hard gelatine capsules. The drug content in one capsule was 25 mg. The dissolution test was performed according USP II. The vessels were filled with 900 mL of 0.1 M HCl containing 0.5% w/v sodium dodecyl sulfate at 37.5° C. The paddle speed was set at 50 rpm during the first 90 minutes, after which the paddle speed was increased to 150 rpm for another 30 minutes. Samples of 10 mL were taken after 0, 5, 10, 20, 30, 45, 60, 90 and 120 minutes, filtered through a 0.22 µm filter. All experiments were performed in triplicate and the mean of these three experiments±the covariance was plotted as function of the time. Drug content in the samples was determined with HPLC. After 20 min approx. 85% of the drug was released.

Example 11

Release Profile PEG 4000 Capsules (SD) of COMPOUND 1

650 mg of the powder produced according to Example 4 was filled into hard gelatine capsules. The drug content in one capsule was 25 mg. The dissolution test was performed according USP II. The vessels were filled with 900 mL of 0.1 M HCl containing 0.5% w/v sodium dodecyl sulfate at 37.5° C. The paddle speed was set at 50 rpm during the first 90 minutes, after which the paddle speed was increased to 150 rpm for another 30 minutes. Samples of 10 mL were taken after 0, 5, 10, 20, 30, 45, 60, 90 and 120 minutes, filtered through a 0.22 µm filter. All experiments were performed in triplicate and the mean of these three experiments±the covariance was plotted as function of the time. Drug content in the samples was determined with HPLC. After 20 min approx. 85% of the drug was released.

Example 12

Release Profile PEG 4000 Tablets (SD) of COMPOUND 1

The drug release from tablets produced according to Example 8 was tested. The drug content per tablet was 25 mg. The dissolution test was performed according USP II. The vessels were filled with 900 mL of 0.1 M HCl containing 0.5% w/v sodium dodecyl sulfate at 37.5° C. The paddle speed was set at 50 rpm during the first 90 minutes, after which the paddle speed was increased to 150 rpm for another 30 minutes. Samples of 10 mL were taken after 0, 5, 10, 20, 30, 45, 60, 90 and 120 minutes, filtered through a 0.22 µm filter. All experiments were performed in triplicate and the mean of these three experiments±the covariance was plotted as function of the time. Drug content in the samples was determined with HPLC. After 20 min approx. 82% of the drug was released.

Example 13

PEG 4000 Tablets of COMPOUND 1 without Spray-drying

In this example, a comparative formulation was prepared in order to compare the release profile of formulations produced according the invention with those of a standard approach (e.g., melt-extrusion). 150 mg of a poorly soluble drug (COMPOUND 1) was weighed in a glass injection vial. Afterwards 2850 mg of a heated (80° C.) surfactant-co-solvent mixture containing 66.67% (w/w) PEG 4000, 16.67% (w/w) Polysorbat 80, and 16.67% (w/w) Solutol® HS 15 was added to this vial. This mixture was stored in an oven at 80° C. until the drug was completely dissolved. The resulting solution was poured onto a glass plate and cooled to 25° C. for solidification. The solid mass was than crushed with a spatula into irregular particles with a diameter of about 2 mm to 5 mm. 3 bifacial tablets with a diameter of 12.5 mm composed of 325 mg crushed solid mass (containing 12.5 mg drug), 325 mg granulated hydrophilic fumed silica (AEROPERL® 300/30, Degussa AG, Germany), and 125 mg polyvinylpyrrolidone (Kollidon® CL, BASF, Germany) were compressed by using an experimental hydraulic press and a compaction pressure of 40 bars applied for 2 sec.

Example 14

Dissolution of PEG 4000 COMPOUND 1 Tablets without Spray-drying

The drug release from tablets produced according to Example 13 was tested. The drug content per tablet was 12.5 mg. The dissolution test was performed according USP II. The vessels were filled with 900 mL of 0.1 M HCl containing 0.5% w/v sodium dodecyl sulfate at 37.5° C. The paddle speed was set at 50 rpm during the first 90 minutes, after which the paddle speed was increased to 150 rpm for another 30 minutes. Samples of 10 mL were taken after 0, 5, 10, 20, 30, 45, 60, 90 and 120 minutes, filtered through a 0.22 μm filter. All experiments were performed in triplicate and the mean of these three experiments±the covariance was plotted as function of the time. Drug content in the samples was determined with HPLC. After 20 min approx. 60% of the drug was released.

Example 15

Liquid Filled Capsules of COMPOUND 1 Based on PEG 4000

In this example, a comparative formulation was prepared in order to compare the release profile of formulations produced according the invention with those of a standard approach (e.g., liquid-filled capsules). 150 mg of a poorly soluble drug (COMPOUND 1) was weighed in a glass injection vial. Afterwards 2850 mg of a heated (80° C.) surfactant-co-solvent mixture containing 66.67% (w/w) PEG 4000, 16.67% (w/w) Polysorbat 80, and 16.67% (w/w) Solutol® HS 15 was added to this vial. This mixture was stored in an oven at 80° C. until the drug was completely dissolved. The resulting solution was filled into hard gelatine capsules (Licaps size 0, Capsugel, Belgium) and cooled down to 25° C. for solidification. Every capsule was filled with 500 mg molten mass (containing 25 mg COMPOUND 1).

Example 16

Dissolution of Liquid Filled COMPOUND 1 Capsules Based on PEG 4000

The drug release from capsules produced according to Example 15 was tested. The drug content per tablet was 25 mg. The dissolution test was performed according USP II. The vessels were filled with 900 mL of 0.1 M HCl containing 0.5% w/v sodium dodecyl sulfate at 37.5° C. The paddle speed was set at 50 rpm during the first 90 minutes, after which the paddle speed was increased to 150 rpm for another 30 minutes. Samples of 10 mL were taken after 0, 5, 10, 20, 30, 45, 60, 90 and 120 minutes filtered through a 0.22 um filter. All experiments were performed in triplicate and the mean of these three experiments±the covariance was plotted as function of the time. Drug content in the samples was determined with HPLC. After 20 min approx. 52% of the drug was released.

Example 17

Preparation of COMPOUND 2 Formulation (SD)

250 mg of the poorly soluble drug COMPOUND 2 was weighed in a glass flask. Afterwards 9.75 g of a surfactant-co-solvent mixture containing 66.34% (w/w) PEG 4000, 16.58% (w/w) Polysorbat 80, 16.58% (w/w) Vitamin E TPGS and 0.5% anhydrous citric acid (w/w) was added to this flask. This mixture was stored in an oven at 80° C. until the drug was completely dissolved. 1 g of this molten solution was mixed with 100 ml of an aqueous hydroxypropyl methylcellulose solution (HPMC Grad E5, 0.016% w/w). The resulting solution was then spray-dried using a Mini Spray Dryer Büchi 191 (Büchi, Switzerland). The airflow was 600 l/h, the inlet temperature was 150° C., the aspirator was set to 80%, the feed flow rate was about 5.5 g/min, the outlet temperature under these conditions was about 90° C. This process was repeated until the complete drug-surfactant-co-solvent mixture was processed. A free-flowable powder was obtained.

Example 18

Tabletting of the SD Powder of COMPOUND 2

650 mg powder produced according to example 17 was mixed with 450 mg granulated hydrophilic fumed silica (AEROPERL® 300/30, Degussa AG, Germany) and 200 mg polyvinylpyrrolidone (Kollidon® CL, BASF, Germany). Then, the mixture was compressed to a bifacial tablet with a diameter of 12.5 mm by using an experimental hydraulic press and a compaction pressure of 40 bars applied for 2 sec.

Example 19

Release Profile PEG 4000 capsules (SD) of COMPOUND 2

The drug release from tablets produced according to Example 18 was tested. The drug content per tablet was 12.5 mg. The dissolution test was performed according USP II. The vessels were filled with 900 mL of 0.1 M HCl containing 0.5% w/v sodium dodecyl sulfate at 37.5° C. The paddle speed was set at 50 rpm during the first 90 minutes, after which the paddle speed was increased to 150 rpm for another 30 minutes. Samples of 10 mL were taken after 0, 5, 10, 20, 30, 45, 60, 90 and 120 minutes, filtered through a 0.22 μm filter. All experiments were performed in triplicate and the mean of these three experiments±the covariance was plotted as function of the time. Drug content in the samples was determined with HPLC. After 20 min approx. 92% of the drug was released.

Example 20

Preparation of COMPOUND 3 Formulation (SD TPGS)

0.2 g of a poorly soluble drug (COMPOUND 3) was weighed in a flask. Afterwards 1.8 g of a heated (80° C.) Vitamin E TPGS containing 0.5% (w/w) anhydrous citric acid was added to this flask. This mixture was stored in an oven at 80° C. until the drug was completely dissolved. 2 g of this molten solution was mixed with 100 ml of an aqueous hydroxypropylmethylcellulose solution (HPMC Grad E5, 0.6% w/w). The resulting solution was then spray-dried using a Mini Spray Dryer Büchi 191 (Büchi, Switzerland). The airflow was 600 l/h, the inlet temperature was 120° C., the aspirator was set to 80%, the feed flow rate was about 5.5 g/min, and the outlet temperature under these conditions was about 80° C. A free-flowable powder was obtained. This Example shows that the present invention is not limited to surfactant-co-solvent mixtures. Once an aqueous micellar solution of the poorly soluble compound was obtained in the presence of a dissolved pharmaceutically acceptable water soluble carrier the resulting micellar solution was processed according to the present invention.

Example 21

Scale up Experiment of COMPOUND 1 Formulation (SD TPGS)

100.0 g of a poorly soluble drug (COMPOUND 1) was weighed in a flask. Afterwards 1900.0 g of a heated (80° C.) Vitamin E TPGS containing 0.5% (w/w) anhydrous citric acid was added to this flask. This mixture was stored in an oven at 80° C. and stirred until the drug was completely dissolved. 2 kg of this molten solution (2000.0 g) was mixed with 18.0 L of an aqueous hydroxypropylmethylcellulose solution (HPMC Grad E5, 3.33% w/w). The resulting micellar solution was then spray-dried using a spray dryer Niro Atomizer Mobile Minor (Niro Inc.). The inlet temperature was 250° C., the feed flow rate was about 50 g/min, and the outlet temperature under these conditions was about 80° C. A free-flowable powder was obtained. This Example shows that a scale up to larger equipment is also possible and resulted in a powder having the same properties as a powder produced on a small lab scale.

Example 22

Measurement of Temperature Stability of Powder Obtained in Example 21 (SD TPGS)

The product of example 21 (large scale production compound 1 SD TPGS) was placed in an oven at 80° C. and kept at 80° C. for 4 weeks. No major changes with regard to the powder morphology were observed. Even after 4 weeks storage at 80° C., a free-flowable powder was still remaining. In contrast, a physical mixture with the same composition was completely molten already after 1 hour storage at 80° C. in the same oven.

Example 23

Comparative Bioavailability Data for 4 Different Formulations of COMPOUND 1 in Male Beagle Dogs A comparative bioavailability study in cross-over design was performed to test the bioavailability of a final dosage form containing embedded micelles according to the present invention versus other formulation types. Four male beagle dogs were administered with 50 mg of compound 1 formulated in several dosage forms as shown in Table 1 below.

TABLE 1

Composition of the investigated formulations

| | Micellar solution | | Micronized tablet | | Liquid filled capsule | | Embedded micelles tablet | |
|---|---|---|---|---|---|---|---|---|
| | (mg) | (%) | (mg) | (%) | (mg) | (%) | (mg) | (%) |
| COMPOUND 1 | 50 | 5 | 25 | 8.33 | 25 | 5 | 25 | 1.72 |
| SDS | | | 0.5 | 0.17 | | | | |
| PVP-CL | | | 30 | 10 | | | 400 | 27.59 |
| HPMC E5 ® | | | 2.5 | 0.83 | | | 150 | 10.34 |
| Vit E TPGS | 945.25 | 94.53 | | | 472.63 | 94.53 | 472.63 | 32.6 |
| Citric acid | 4.75 | 0.48 | | | 2.37 | 0.47 | 2.37 | 0.16 |
| Pruv ® | | | 1.5 | 0.5 | | | | |
| MCC | | | 240.5 | | 80.17 | | | |
| Aeropearl 300 ® | | | | | | | 400 | 27.59 |
| Total | 100 | 100 | 300 | 100 | 500 | 100 | 1450 | 100 |

Figure 2:
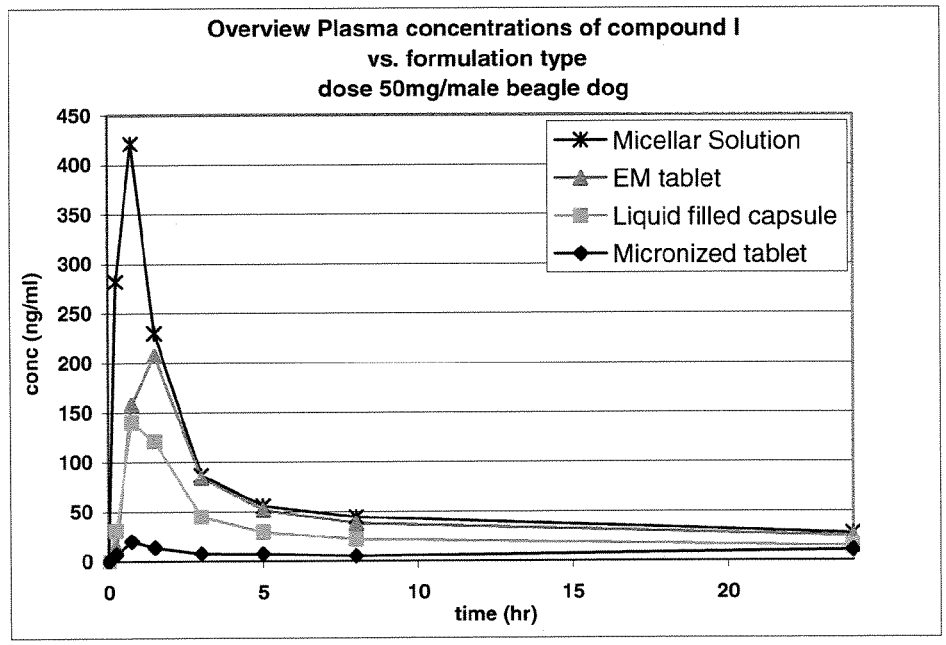
FIG. 2 is a graph that illustrates the plasma concentrations of COMPOUND 1 obtained after administering four different formulations, including the formulation according to the present invention, to male beagle dogs.

In all cases 50 mg of COMPOUND 1 has been administered, meaning that in some cases two dosage forms were administered simultaneously. The mean plasma levels after oral administration measured according to the method described in Example 1 are depicted in FIG. 2. From these measurements the data as given in Table 2 was obtained.

TABLE 2

Results of the comparative bioavailability study for COMPOUND 1 in male beagle dogs

| Formulation type | Cmax ratio | Relative bioavailability |
|---|---|---|
| Micellar solution | 18 | 7.6 |
| Tablet (micronized) | 1 | 1 |
| Liquid filled capsule | 8 | 3.5 |
| Embedded micelles tablet | 10 | 5.7 |

As shown above, the relative bio-availability in male beagle dogs of the composition according to the present invention, for example a tablet comprising embedded micelles containing an active compound, was about 6 times higher as compared with the relative bio-availability of a tablet containing a micronized active compound.

What is claimed is:

1. A solid composition comprising nanosized micelles, wherein said micelles comprise a poorly soluble active substance dissolved in an auxiliary material or a mixture of auxiliary materials,
   wherein said auxiliary material or said mixture of auxiliary materials is chosen from polyoxyethylene stearates, Polyoxyethylene sorbitan fatty acid esters, Polyoxyethylene Castor Oil Derivatives, Vitamin E TPGS, nonionic polyoxyethylene-polyoxypropylene block co-polymers, water-soluble long chain organic phosphate esters, and inulin lauryl carbamate,
   wherein said micelles are embedded in a water-soluble carrier, wherein said water-soluble carrier is chosen from:
      alkylcelluloses;
      hydroxyalkylcelluloses;
      hydroxyalkyl-alkylcelluloses;
      carboxyalkylcelluloses;
      alkali metal salts of carboxyalkylcelluloses;
      carboxyalkylalkylcelluloses;
      starches;
      pectines;
      chitin derivates;
      polysaccharides, alkali metal and ammonium salts thereof;
      carrageenans, galactomannans, tragacanth, agar-agar, gummi arabicum, guar gummi, and xanthan gummi;
      polyacrylic acids and the salts thereof;
      polymethacrylic acids and the salts thereof, methacrylate copolymers;
      polyvinylalcohol;
      polvinylpyrrolidone, copolymers of polyvinylpyrrolidone with vinyl acetate;
      polyalkylene oxides; and
      copolymers of ethylene oxide and propylene oxide; and
   wherein the composition is a powder that remains free flowing when heated above the melting point of the main auxiliary material.

2. The composition according to claim 1, wherein said micelles have an effective average particle size of less than about 1000 nm.

3. The composition according to claim 2, wherein said micelles have an effective average particle size of less than about 500 nm.

4. The composition according to claim 1, wherein said micelles have an effective average particle size of less than about 1000 nm.

5. The composition according to claim 4, wherein said micelles have an effective average particle size of less than about 500 nm.

6. The composition according to claim 1, wherein said auxiliary material or said mixture of auxiliary materials comprises at least 10% w/w of a surfactant and optionally one or more co-solvents and/or one or more co-surfactants.

7. The composition according to claim 6, wherein said co-solvent is chosen from alkylene glycols, polyhydric alcohols, linear polyols, and mixtures thereof.

8. The composition according to claim 7, wherein said co-solvent is Polyethylene Glycol (PEG).

9. The composition according to claim 8, wherein said co-solvent is Polyethylene Glycol (PEG) having a molecular weight equal to or less than 800 Daltons.

10. The composition according to claim 8, wherein said co-solvent is Polyethylene Glycol (PEG) having a molecular weight ranging from 950 to 20,000 Daltons.

11. The composition according to claim 1, wherein the composition is in the form of a powder, granules, a compressed tablet, a sublingual tablet, a buccal tablet, a filled capsule, or a filled sachet.

12. The composition according to claim 1, wherein said poorly soluble active substance is chosen from cannabinoid agonists, cannabinoid inverse agonists and cannabinoid antagonists.

13. The composition according to claim 12, wherein said poorly soluble active substance is (4S)-3-(4-chlorophenyl)-4,5-dihydro-N-methyl-4-phenyl-N'-(1-piperidinyl-sulfonyl) - 1H-pyyrazole-1-carboximidamide.

14. The composition according to claim 12, wherein said poorly soluble active substance is (4S)-3-(4-chlorophenyl)-N-[(4-chlorophenyl)sulfonyl]-4,5-dihydro-N'-methyl-4-phenyl -1H-pyrazole-1-carboximidamide.

15. The composition according to claim 12, wherein said poorly soluble active substance is (4S)-3-(4-chlorophenyl)-4,5-dihydro-N-methyl-4-phenyl-N'-[[4-(trifluoromethyl)-phenyl]sulfonyl]-1H-pyrazole-1-carboximidamide.

16. A process for preparing a solid pharmaceutical composition, comprising:
   A) combining a poorly soluble active substance, an auxiliary material or a mixture of auxiliary materials, optionally one or more additional auxiliary materials, a matrix forming material, and water to form nanosized micelles; and
   B) drying the mixture obtained in (A) to obtain a solid pharmaceutical composition, wherein the micelles are embedded in the matrix forming material, and wherein the composition is a powder that remains free flowing when heated above the melting point of the main auxiliary material;
   wherein said auxiliary material or said mixture of auxiliary materials is chosen from polyoxyethylene stearates, Polyoxyethylene sorbitan fatty acid esters, Polyoxyethylene Castor Oil Derivatives, Vitamin E TPGS, nonionic polyoxyethylene-polyoxypropylene block co-polymers, water-soluble long chain organic phosphate esters, and inulin lauryl carbamate; and
   wherein said water-soluble carrier is chosen from:
      alkylcelluloses;
      hydroxyalkylcelluloses;
      hydroxyalkyl-alkylcelluloses;
      carboxyalkylcelluloses;
      alkali metal salts of carboxyalkylcelluloses;
      carboxyalkylalkylcelluloses;
      starches:
      pectines;
      chitin derivates;
      polysaccharides, alkali metal and ammonium salts thereof;
      carrageenans, galactomannans, tragacanth, agar-agar, gummi arabicum, guar gummi, and xanthan gummi;
      polyacrylic acids and the salts thereof;
      polymethacrylic acids and the salts thereof, methacrylate copolymers;
      polyvinylalcohol;
      polvinylpyrrolidone, copolymers of polyvinylpyrrolidone with vinyl acetate;
      polyalkylene oxides; and
      copolymers of ethylene oxide and propylene oxide.

17. The process according to claim 16, wherein the combining of step (A) comprises:
(a) dissolving the poorly soluble active substance in the auxiliary material or the mixture of auxiliary materials;
(b) optionally adding one or more additional auxiliary materials to the solution obtained in (a);
(c) mixing the solution obtained in (a) or (b) with water to form the nanosized micelles; and
(d) dissolving the matrix forming material in the mixture obtained in (c).

18. The process according to claim 16, wherein step the combining of step (A) comprises:
(a) dissolving the poorly soluble active substance in the auxiliary material or the mixture of auxiliary materials;
(b) optionally adding one or more additional auxiliary materials to the solution obtained in (a);
(c) dissolving the matrix forming material in water; and
(d) mixing the solution obtained in (a) or (b) with the solution obtained in (c) to form the nanosized micelles.

19. The process according to claim 16, wherein the combining of step (A) comprises:
(a) dissolving the poorly soluble active substance in the auxiliary material or the mixture of auxiliary materials;
(b) dissolving the solution obtained in (a) in water to form the nanosized micelles;
(c) optionally adding one or more additional auxiliary materials to the solution obtained in (b); and
(d) dissolving the matrix forming material in the mixture obtained in (b) or (c).

20. The process according to claim 16, wherein the combining of step (A) comprises:
(a) dissolving the auxiliary material or the mixture of auxiliary materials in water;
(b) dissolving the poorly soluble active substance in the solution obtained in (a);
(c) optionally adding one or more additional auxiliary materials to the solution obtained in (b), wherein the solution obtained in (b) or (c) contains micelles comprising the poorly soluble active substance; and
(d) dissolving the matrix forming material in the solution obtained in (b) or (c).

21. The process according to claim 16, wherein said drying of (B) is performed by freeze drying, spray drying, freeze spray drying, vacuum drying, or a combination thereof.

22. The process according to claim 16, further comprising processing said solid pharmaceutical composition into granules, a compressed tablet, a sublingual tablet, a buccal tablet, or filling a capsule or sachet with said solid pharmaceutical composition.

* * * * *

UNITED STATES PATENT AND TRADEMARK OFFICE
CERTIFICATE OF CORRECTION

| | | |
|---|---|---|
| PATENT NO. | : 7,923,026 B2 | Page 1 of 1 |
| APPLICATION NO. | : 11/875328 | |
| DATED | : April 12, 2011 | |
| INVENTOR(S) | : Jan Peter Möschwitzer | |

It is certified that error appears in the above-identified patent and that said Letters Patent is hereby corrected as shown below:

Claim 18, col. 23, line 11, delete "step" after --wherein--.

Signed and Sealed this
Twenty-third Day of August, 2011

David J. Kappos
*Director of the United States Patent and Trademark Office*